(12) United States Patent
Laby et al.

(10) Patent No.: US 9,055,938 B2
(45) Date of Patent: Jun. 16, 2015

(54) SURGICAL SUTURING LATCH

(71) Applicant: Boss Instruments, Ltd., Inc., Incline Village, NV (US)

(72) Inventors: Keith Phillip Laby, San Francisco, CA (US); Patricia A. Moore, Incline Village, NV (US)

(73) Assignee: Boss Instruments, Ltd., Inc., Gordonsville, VA (US)

(*) Notice: Subject to any disclaimer, the term of this patent is extended or adjusted under 35 U.S.C. 154(b) by 0 days.

(21) Appl. No.: 13/863,213

(22) Filed: Apr. 15, 2013

(65) Prior Publication Data
US 2013/0231687 A1    Sep. 5, 2013

Related U.S. Application Data

(62) Division of application No. 12/687,349, filed on Jan. 14, 2010, now Pat. No. 8,419,754.

(60) Provisional application No. 61/145,390, filed on Jan. 16, 2009.

(51) Int. Cl.
*A61B 17/04*  (2006.01)
*A61B 17/062* (2006.01)
*A61B 17/00*  (2006.01)
*A61B 17/28*  (2006.01)
*A61B 17/29*  (2006.01)

(52) U.S. Cl.
CPC ......... *A61B 17/0469* (2013.01); *A61B 17/0482* (2013.01); *A61B 17/062* (2013.01); *A61B 2017/0046* (2013.01); *A61B 2017/00464* (2013.01); *A61B 2017/00473* (2013.01); *A61B 17/28* (2013.01); *A61B 17/29* (2013.01); *A61B 17/0491* (2013.01); *A61B 2017/00477* (2013.01)

(58) Field of Classification Search
CPC ........... A61B 17/0469; A61B 17/0482; A61B 17/0491; A61B 17/062; A61B 2017/0046; A61B 2017/00464; A61B 2017/00473
See application file for complete search history.

(56) References Cited

U.S. PATENT DOCUMENTS

| | | | |
|---|---|---|---|
| 8,419,754 B2 * | 4/2013 | Laby et al. | 606/144 |
| 2007/0060931 A1 * | 3/2007 | Hamilton et al. | 606/144 |
| 2008/0046003 A1 * | 2/2008 | Renger et al. | 606/206 |
| 2008/0243147 A1 * | 10/2008 | Hamilton et al. | 606/144 |

* cited by examiner

Primary Examiner — Jonathan W Miles
Assistant Examiner — Todd J Scherbel
(74) Attorney, Agent, or Firm — Williams Mullen, PC; Joshua B. Brady

(57) ABSTRACT

Suturing systems may comprise a cartridge and a drive unit which are detachable from each other. The cartridge often has a cartridge body, a plurality of jaws, and a cartridge interface. The drive unit has a drive unit body, a linkage, and a drive unit interface which will typically include a latch. A latch input is coupled to the latch so that a movement of the input moves the latch to the released position. The cartridge interface or the drive unit interface includes a channel while the other includes a shaft which is fittingly receivable in the channel. Opposed motions of the input and cartridge during cartridge removal avoid inadvertent detachment during use.

16 Claims, 8 Drawing Sheets

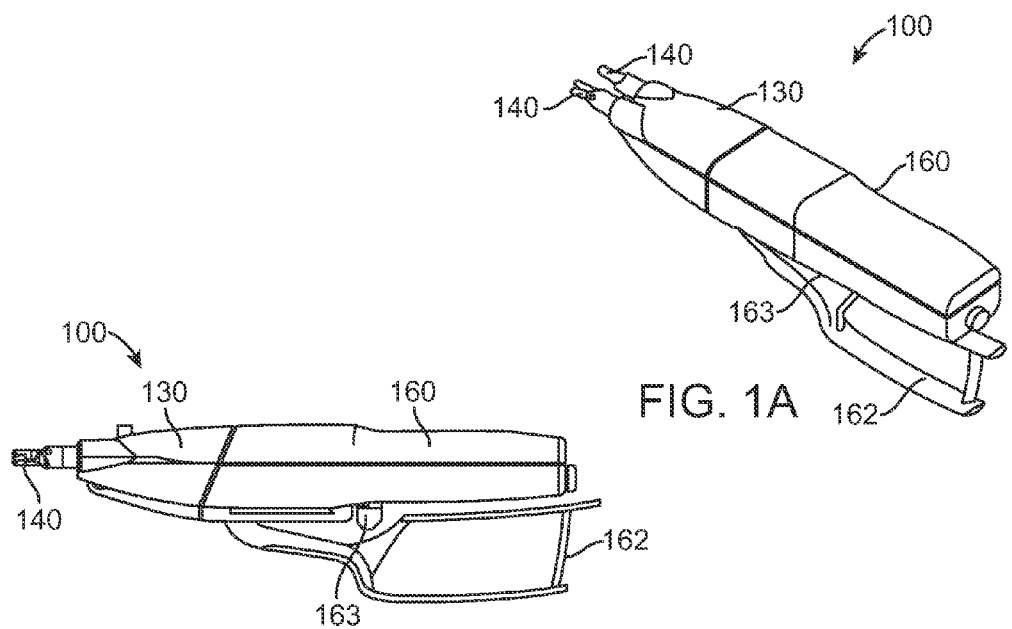
FIG. 1A
FIG. 1B
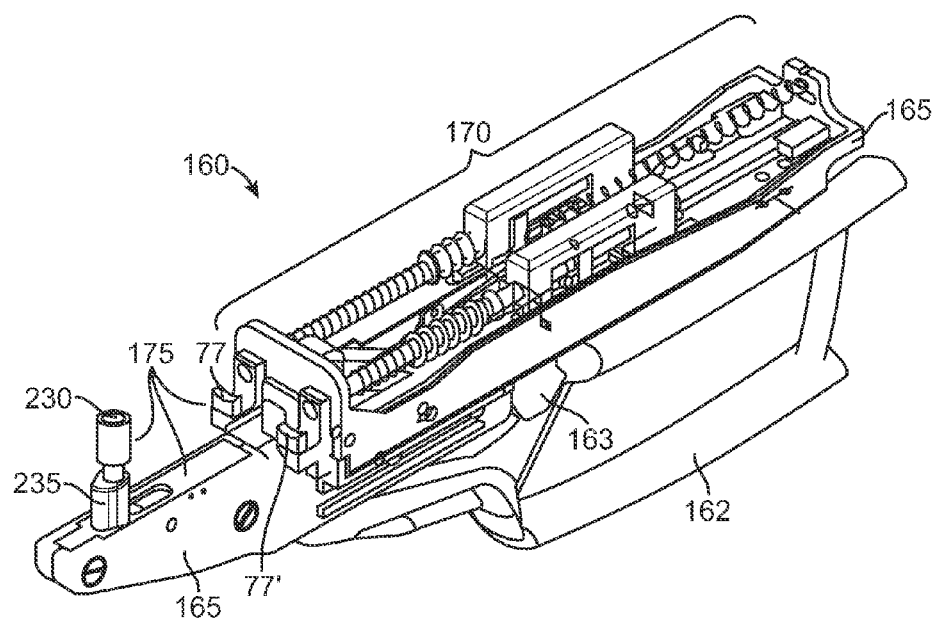
FIG. 2

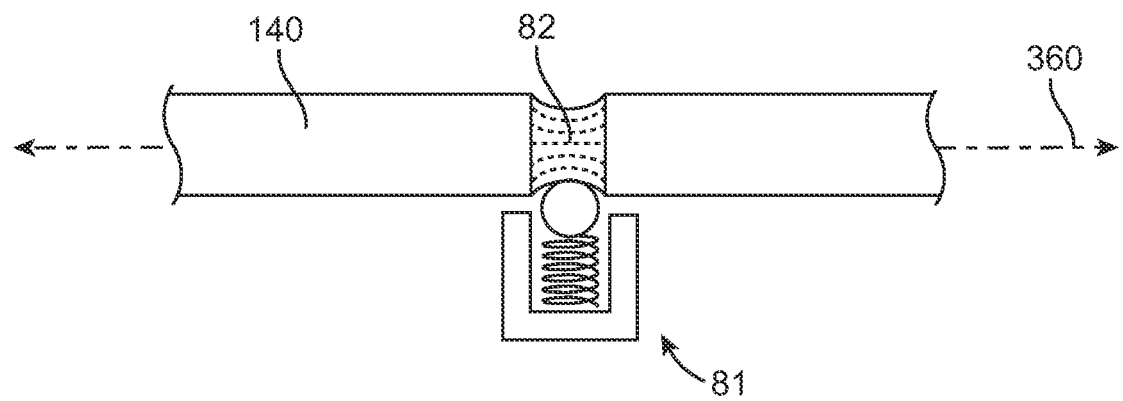
FIG. 3A1

SURGICAL SUTURING LATCH

CROSS REFERENCE TO RELATED APPLICATION DATA

This patent application is a divisional of U.S. patent application Ser. No. 12/687,349, filed Jan. 14, 2010 (now U.S. Pat. No. 8,419,754), which claims the benefit under 35 USC 119(e) of U.S. Provisional Application No. 61/145,390 filed Jan. 16, 2009; the full disclosures of which are incorporated herein by reference in their entirety.

BACKGROUND OF THE INVENTION

The present invention generally relates to medical devices, systems, and methods. In specific embodiments, the invention provides devices, systems, and methods for suturing tissues in open surgery, minimally invasive surgical procedures, and the like. In particular, many embodiments of the invention provide suturing systems and devices which have parts that are removable from each other.

Although many aspects of surgery have changed radically over the last several decades, some surgical techniques have remained remarkably constant. For example, as was true fifty years ago, suturing remains a common technique for approximation of tissues, ligation of tissues, affixing tissues together, and the like.

Suture has been used in open surgical procedures for generations to therapeutically treat diseased tissue and to close surgical access sites and other wounds. More recently, the use of minimally invasive surgical techniques has expanded, with surgical therapies often being performed at internal surgical sites. Although a wide variety of visualization techniques (including laparoscopes and other endoscopic viewing devices, fluoroscopy and other remote imaging modalities, and the like) have been developed to allow surgeons to view these internal surgical sites, and although a large variety of new tissue treatment techniques have been developed (including ultrasound techniques, electrosurgical techniques, cryosurgical techniques, and the like) and are now widely available, many modern surgical interventions continue to rely on suturing.

A wide variety of alternatives to suturing of tissues have been developed, and have gained varying degrees of acceptance in certain surgical procedures. Staples and tissue adhesives are used quite frequently in many open and minimally invasive surgical settings, and a variety of tissue welding techniques have also been proposed. Nonetheless, suturing remains ubiquitous in surgery, as suturing provides a number of advantages over many of the alternatives.

Suture's advantages include the large knowledge and skill base that surgeons have developed over the years. Additionally, a variety of off-the-shelf, pre-packaged surgical needles with suture are available from a large number of suppliers at very reasonable cost. Surgeons are able to precisely control the location of suture stitches by grasping the suture needle and first pushing it and then pulling it through the target tissue. In open surgery, the surgeon may manually grasp the suture needle directly with his or her hand, although both open and minimally invasive procedures are often performed by grasping the needle with a needle grasping tool and manipulating the tool to place the suture stitches. The results obtained using suture are highly predictable, although dependent on the skill of the surgeon. In light of its advantages, the use of suture does not appear likely to disappear any time soon, with even modern robotic surgical techniques often making use of suture.

Although suture remains popular in surgery at least in part due to its significant advantages, suturing is not without disadvantages. In particular, placing a large number of suture stitches can be tiring and quite time-consuming. Manipulation of a suture needle can be difficult even in open surgery due to the limited space that is often available around the target tissues. The challenges of manipulating suture needles may be even greater in minimally invasive surgical procedures, where the needles are often manipulated using long-handled tools extending through a small aperture, typically while viewing the procedure on a display which is offset from the surgical site. Tying knots with a desired amount of tension and the like may call for intricate and precise manipulation of the suture, further complicating and delaying open and minimally-invasive surgeries. In fact, the time spent closing/suturing the access site may be significantly greater than the time spent treating the underlying target tissues for many procedures. Additionally, repeated needle manipulations associated with stitches and knot tying may increase the needle stick risk—an inadvertent needle puncture to the surgeon or other member of the surgical team. Such needle sticks can increase the risk of infection to the surgical staff and patient.

There have been a variety of proposals for modifications to standard surgical suturing structures and methods to try to address the above disadvantages. At least some of these proposals may seek to rely on specialized and/or proprietary suturing needle systems, which could increase costs and preclude their wide acceptance, especially in third world countries. Unfortunately, many proposals for modifying existing suturing techniques may also decrease the surgeon's control over the placement of the suture, such as by relying on an automated or indirect mechanical movement of a device to drive a suture needle into and/or through tissues. While these new proposals have in the past or may in the future gain varying degrees of acceptance in one or more surgical procedures, standard suturing techniques continue to predominate throughout surgery in general.

In light of the above, it would be desirable to provide improved suturing devices, systems, and methods. It would be generally desirable to maintain some, most, or all of the advantages of standard suturing techniques, preferably while decreasing the time required for suturing, the strain on the surgeon, the needle stick risk, the training involved in achieving competence or time-efficiency in suturing techniques, or the like. It would be particularly advantageous if these improvements could be provided without requiring extensive capital investments for new equipment, without significant increases in complexity of the suturing process, or without having to resort to specialized or proprietary suturing needles and the like. Such suturing systems would be particularly beneficial if they were configured to maintain or even enhance the sterile surgical field, the components ideally being configured for safe and cost effective sterilization techniques without degrading their ease of use, without excessive risk of inadvertent system malfunction during a surgical procedure, and while reducing the risk of the surgeon or operator of being pricked by a suturing needle.

BRIEF SUMMARY OF THE INVENTION

Embodiments of the present invention provide improved suturing systems and methods that maintain some or all of the advantages of standard open and/or minimally invasive suturing techniques while providing enhanced speed, ease of use, convenience, reduced disease transmission risk, and ease of cleaning and sterilization. Exemplary suturing systems of the present invention will generally include a cartridge and a drive unit. The cartridge has a cartridge body, a plurality of needle grasping jaws, and a cartridge interface. The drive unit has a drive unit body, a linkage, and a drive unit interface. The drive unit interface and/or the cartridge interface will often include a latch that can hold the cartridge interface in engagement with the drive unit interface, and a released position for releasing the cartridge from the drive unit. A latch input is coupled to the latch so that a movement of the input moves the latch to the released position. The interfaces can be configured so that removal of the cartridge from the drive unit involves two opposed motions relative to the drive unit, such as pressing the input along a first direction while simultaneously pulling the cartridge away from the drive unit in a second direction substantially opposed to the first direction. Alternative cartridge embodiments may be removed by simultaneously pressing opposed inputs on the sides of the cartridge toward each other while pulling the cartridge away from the drive unit, or the like. Preferably, the cartridge interface or the drive unit interface includes a channel and the other includes a shaft which is fittingly receivable in the channel. The input may be mounted to the shaft so that the input is accessible beyond the channel of the cartridge body.

In a first aspect, the invention provides a suturing system for use with a needle. The suturing system comprises a cartridge and a drive unit. The cartridge has a cartridge body, a plurality of jaws, and a cartridge interface. The drive unit has a drive unit body, a linkage, and a drive unit interface. The cartridge interface is removably mountable to the drive unit interface. Cycling of the linkage effects alternating grasping of the needle by the jaws when the drive unit interface engages the cartridge interface and the needle is positioned for use. The drive unit interface or the cartridge interface includes a latch. The latch has at least two positions: a latched position maintaining the cartridge interface in engagement with the drive unit interface, and a released position releasing the cartridge from the drive unit. A latch input is coupled to the latch so that two opposed motions (each comprising a motion relative to the drive unit body) effect movement of the latch to the released position and removal of the cartridge from the drive unit.

In many embodiments, it is the drive unit interface which includes the latch. The cartridge interface is removable from the drive unit interface along a removal orientation, and the latch input is often coupled to the latch so that a movement of the input moves the latch to the released position. The movement of the input is along a mounting orientation so that removal of a latched drive unit involves opposed motions, relative to the drive unit body, of the input and cartridge.

Typically, the cartridge interface or the drive unit interface includes a channel and the other includes a shaft and a column, the column supporting and axially receiving a portion of the shaft. The channel axially receives the shaft and/or the column along the mounting orientation. Movement of the cartridge along the mounting orientation effects movement of the latch to the latched position. The jaws may be included in a clamping assembly that reciprocates along an associated jaw reciprocation axis during cycling of the linkage. The jaw reciprocation axes are disposed transverse to the mounting orientation, e.g., jaw reciprocation axes are orthogonal or oblique to the mounting orientation. The shaft and the column may be included in the drive unit interface, and the channel may be included in the cartridge interface with the channel extending through the cartridge body, and the input may be mounted to the shaft so that the input is accessible beyond the channel of the cartridge body.

In many embodiments, the latch is included in an interface assembly that is detachably mounted to the drive unit body. This facilitates sterilization and/or replacement of the interface assembly independently of at least a portion of the linkage.

In another aspect, embodiments of the invention provide a suturing system for use with a needle. The suturing system comprises a cartridge and a drive unit. The cartridge has a cartridge body, a plurality of jaws, and a cartridge interface including a channel through the cartridge body. The drive unit has a drive unit body, a linkage, and a drive unit interface including a latch and a shaft assembly fittingly receivable within the channel along a mounting orientation. Cycling of the linkage effects alternating grasping of the needle by the jaws when the drive unit interface engages the cartridge interface and the needle is positioned for use. The latch has a latched position maintaining the cartridge interface in engagement with the drive unit interface, and a released position releasing the cartridge from the drive unit. A latch input extends along the shaft assembly of the drive unit interface so that the latch input is accessible through the channel of the cartridge and so that articulation of the input transmits motion along the shaft to the latch.

In another aspect, embodiments of the invention provide a suturing drive unit for use with a needle in needle suturing system, the suturing system including a cartridge having a cartridge body, a plurality of jaws, and a cartridge. The suturing drive unit comprises a drive unit having a drive unit body, a linkage, and a drive unit interface. The drive unit interface includes a latch. The cartridge interface is removable from the drive unit interface along a removal orientation. Cycling of the linkage effecting alternates grasping of the needle by the jaws when the drive unit interface engages the cartridge interface and the needle is positioned for use. The latch has a latched position maintaining the cartridge interface in engagement with the drive unit interface and a released position releasing the cartridge from the drive unit. A latch input is coupled to the latch so that a movement of the input moves the latch to the released position. The movement of the input is along a mounting orientation so that removal of a latched drive unit involves opposed motions, relative to the drive unit body, of the input and cartridge.

The cartridge may include a channel through the cartridge body. The drive unit interface may include a shaft fittingly receivable in the channel along the mounting orientation. The input may be mounted to the shaft so that the input is accessible beyond the channel of the cartridge body. The drive unit interface may further include a column supporting and axially receiving a portion of the shaft.

In many embodiments, the latch is included in a latch mechanism. The latch mechanism engages the drive unit interface as the drive unit advances along the mounting orientation so as to effect movement of the latch to the latched position in response to movement of the cartridge relative to the drive unit.

The latch may be included in an interface assembly that is detachably mounted to the drive unit body. Having a detachably mounted interface assembly facilitates sterilization and/or replacement of the interface assembly independently of at least a portion of the linkage.

In another aspect, embodiments of the invention may provide a suturing cartridge for use with a needle in a suturing system, the suturing system includes a drive unit having a linkage, a drive unit interface including a latch, and a shaft assembly with an input. The cartridge comprises a cartridge body, a plurality of jaws, and a cartridge interface. The plurality of jaws is supported by the cartridge body so that cycling of the linkage effects alternating grasping of the needle by the jaws when the cartridge is mounted to the drive unit and the needle is positioned for use. The cartridge interface includes a channel and a latch receiving surface. The channel fittingly receives the shaft assembly along a mounting orientation. The latch receiving surface is engageable by the latch so as to restrain the cartridge interface in engagement with the drive unit interface, and so that actuation of the input is transmitted through the channel so as to release the cartridge from the drive unit.

Movement of the cartridge along the mounting orientation can effect movement of the latching surface to the latched position.

The jaws may each be included in a clamping assembly that reciprocates along an associated jaw reciprocation axis during cycling of the linkage. The jaw reciprocation axes are disposed transverse to the mounting orientation.

The input may be mounted to the shaft so that the input is accessible beyond the channel of the cartridge interface.

In another aspect, embodiments of the invention may provide a method for suturing. A cartridge is mounted to a drive unit along a mounting orientation. The cartridge is latched onto the drive unit. A needle is grasped with a first jaw of the cartridge. A linkage of the drive unit is cycled so as to alternatingly grasp the needle with the first jaw and a second jaw of the cartridge. The cartridge is detached from the drive unit by pushing a latch input of the drive unit along the mounting orientation. The cartridge is moved away from the drive unit along a removal orientation opposing the mounting orientation.

To mount the cartridge, a shaft of the drive unit may be fittingly inserted into a channel of the cartridge until a latch mechanism moves a latch to a latched position, restraining an interface of the cartridge against an interface of the drive unit. The input may be mounted to the shaft so that the input is accessible beyond the channel of the cartridge body, and so that the pushing of the input transmits movement along the shaft to move the latch to a released position. An interface assembly may be detached from a drive unit body and the linkage of the drive unit to facilitate sterilization and/or replacement of the interface assembly independently of at least a portion of the linkage. The interface assembly may include the latch mechanism.

In many embodiments, the jaws are reciprocated along an axis transverse relative to the mounting orientation so that, when not grasping the needle, the jaws are free of tissue. The jaws alternatingly grasp a proximal portion of the needle so as to allow the needle to be inserted distally into a tissue, and a distal portion of the needle so as to allow the needle to be pulled distally from the tissue.

In yet another aspect, the invention provides a suturing system for use with a needle. The suturing system comprises a cartridge unit having a cartridge unit body, a plurality of jaws, and a cartridge unit interface. A drive unit has a drive unit body, an articulatable handle, a linkage, and a drive unit interface. The cartridge unit interface is removably mountable to the drive unit interface so that cycling of the articulatable handle cycles the linkage and the linkage effects alternating grasping of the needle by the jaws when the drive unit interface engages the cartridge unit interface and the needle is positioned for use. A fixed handle surface extends continuously along the drive unit body beyond the interfaces and onto the cartridge. The handle surface is configured for ergonomic grasping by a hand of the user while the hand engages both the cartridge body adjacent the clamp assemblies and the drive body. This positioning of the hand allows the fingers of the hand to manipulate the articulatable handle, such that when the user forms a suture stitch in an open surgical environment by moving the suturing system and articulating the articulatable handle with the hand no assistance of any other hand is needed. Note that another hand may optionally be used when mounting or de-coupling the cartridge from the drive unit. In some embodiments another hand may be employed when tying a knot or the like, though other embodiments will effect knot tying and/or forming of a plurality of suture stitches with only the one hand engaging the suture system and thereby manipulating the suture needle and suture.

BRIEF DESCRIPTION OF THE DRAWINGS

FIG. 1A shows a perspective view of an exemplary suturing system according to embodiments of the invention;

FIG. 1B shows a side view of the suturing system of FIG. 1A;

FIG. 2 shows a perspective view of an exemplary drive unit of the suturing system of FIG. 1A;

FIG. 3A1 shows a ball and detent arrangement of the cartridge of FIG. 3;

DETAILED DESCRIPTION OF THE INVENTION

Figure 2A:
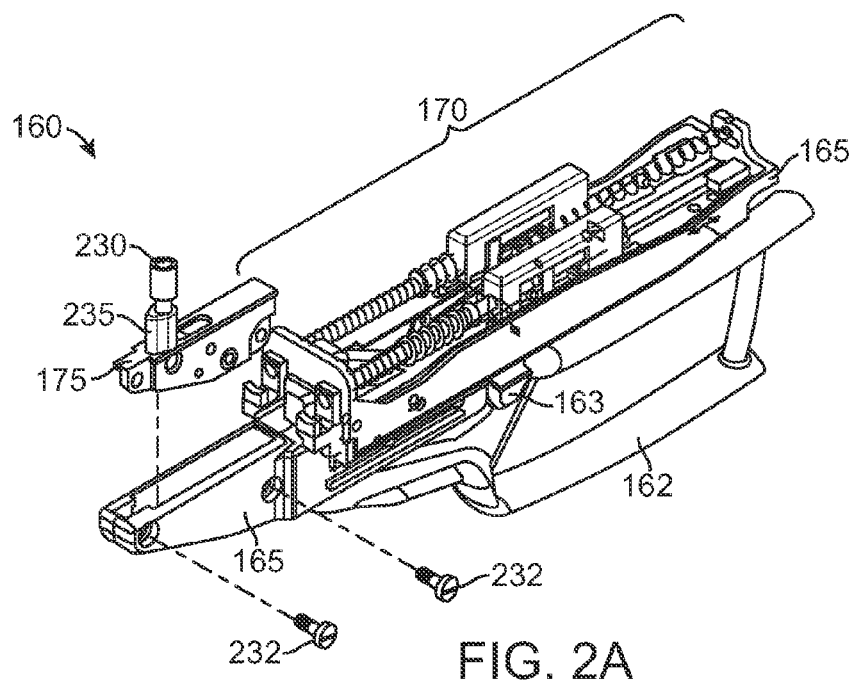
FIG. 2A shows an exploded view of the drive unit of FIG. 2.

The present invention is generally directed to improved medical suturing devices, systems, and methods. Exemplary embodiments of the invention provide improved suturing devices and methods for suturing tissues that can significantly increase the speed and ease of suturing, particularly when suturing of long incisions or where large numbers of stitches are to be deployed, and that have easily removable parts for ease of cleaning and sterilization.

The invention should find a wide variety of applications for stitching anatomical tissues in both humans and animals. Along with endoscopic operations (for example, in laparoscopy) these structures and methods may find use in other areas of surgery where tissues are to be stitched, providing particular advantages for stitching of large incisions by increasing the ease and speed with which each individual stitch may be placed, as well as facilitating and expediting the formation of knots in the suture. The suturing devices and associated methods described herein may, for example, be used suture a wide variety of strata of anatomical tissues, including (but not limited to) subcutaneous layers, fascia, the outer skin, various organs (including the uterus), and the like. While exemplary embodiments are set forth below, these suturing devices and methods may be applicable to a wide variety of suturing operations, including open surgery, large and small cavity procedures, endoscopic procedures, microsurgeries (including for suturing of veins, arteries, and the like), and many specialized surgeries. Embodiments of these devices and methods may be particularly useful for surgeries involving long incisions, including plastic surgeries. A wide variety of blood vessels, including both veins and arteries, may also be stitched using the techniques described herein, for formation of anastomoses and the like. Along with increasing the speed and/or ease of forming surgical suture stitches, embodiments of the invention will often maintain the control a doctor has over the placement of the sutures by maintaining a fixed relationship between the movements of the doctor's hand and the insertion and withdrawal of the suturing needle. Hence, among the procedures which may benefit from the invention are subcuticular peritoneum, fascia closure, and skin closure.

While embodiments of the invention may include (or be used within) a powered or automated system, optionally making use of electromechanical power, hydraulic power, or the like (for example, with some embodiments being included within a robotic system), other embodiments may be configured for manual manipulation by one or more hands of a surgeon, often without having to resort to complex subsystems or external power.

Many embodiments of the devices described herein will be sterilizable so as to allow repeated use. Embodiments of the devices may also comprise components which are easily removable from each other so as to facilitate sterilization and cleaning. Sterilization may be effected using autoclave techniques, chemical sterilization, irradiation, or the like, with most or all of the structures of the suturing device being formed of materials suitable for repeated sterilization (such as stainless steel, other metals and alloys, and the like). In general, the suturing device may comprise one or more plastics and/or metals common to surgical devices. Although specialized or proprietary suturing needles may be employed in some embodiments (for example, needles having flat gripping surfaces so as to maintain an alignment between the needle and an associated clamp), many embodiments of the suturing device will be suitable for use with standard off-the-shelf suture needles such as those packaged with any of a wide variety of permanent or resorbable suture materials in a hermetically sealed package. Some embodiments of the device may even comprise components that are removable and disposable after use and that may be provided sterilized and in a hermetically sealed package. Other embodiments may employ different sterilization techniques for one assembly (such as a cartridge) than that used for another assembly (such as a handle and drive unit). Thus, the invention may find some of its most immediate applications for facilitating surgical procedures performed manually in Third World countries, allowing physicians to treat a larger number of patients with greater ease and safety than can be done using standard suturing techniques, but without the cost or complexity of recently-proposed automated suturing systems.

Referring now to FIGS. 1A and 1B, an exemplary suturing system 100 comprises a cartridge 130 and a drive unit 160. Cartridge 130 includes the articulating jaw assemblies 140 which grasp the suture needle during use. Typically, cartridge 130 is disposable and can be easily removed from drive unit 160 for replacement. Drive unit 160 will typically be reusable. By having cartridge 130 and drive unit 160 removable from each other, drive unit 160 can avoid any need for sterilization, thus avoiding the associated cost. Also, a new cartridge 130 can be provided for use with a single patient and then disposed of, thus increasing the cleanliness and safety of the suturing system 100 when used with each new patient. Cartridge 130 will typically be sterilized and packaged within a hermetically sealed package. Drive unit 160 can be used multiple times with a plurality of cartridges 130.

Cartridge 130 comprises clamp or jaw structures 140. Each clamp or jaw structures 140 will typically be removably coupled to drive unit 160, in particular, to a linkage or linkage mechanism 170 of drive unit 160. Each clamp or jaw structure 140 can be actuated by drive unit 160, for example, by actuation of handle 162 of drive unit 160 to cycle a linkage 170 of drive unit 160. Actuation of clamps such as jaws 140 to suture tissue and linkage mechanisms are described in co-assigned U.S. patent application Ser. No. 11/532,032, entitled "Suturing Device, System, and Method" and filed Sep. 14, 2006, the contents of which are incorporated in their entirety herein by reference. As cartridge 130 includes a pair of jaw or clamp assemblies, the cartridge may sometimes be referred to as a clamp unit, and the portions of the jaw assemblies associated with effecting articulation and movement of the jaws may optionally be analyzed as a portion of the overall drive linkage of the assembled device or system 100. The use of differing cartridges or clamp units is described in U.S. application Ser. No. 12/049,545 entitled "Replaceable Tip Suturing Devices" and filed on Mar. 17, 2008; the full disclosure of which is incorporated herein by reference.

FIG. 2 shows a perspective view of drive unit 160. The top cover of drive unit 160 is not shown for clarity. Drive unit 160 comprises an articulatable handle 162, drive unit body 165, linkage or linkage mechanism 170, and drive unit interface 175. Cartridge 130 can be coupled to drive unit 160 through drive unit interface 175. When cartridge 130 and drive unit 160 are coupled, each clamp or jaw assembly 140 is coupled to drive linkage mechanism 170 via corresponding drive interface surfaces 77 and jaw interface surfaces 79 (see FIGS. 2A and 3A). In at least some cases, drive unit 160 may further comprise a toggle 163, and drive unit 160 may comprise a release mechanism within the linkage so that pressing toggle 163 laterally (with the specific lateral direction depending on which clamp is grasping the needle) moves a surface of the release mechanism so as to release a latch holding the currently grasping jaw assembly in the grasping configuration, as can be understood with reference to application Ser. No. 11/532,032. This results in both clamps being opened so that the needle is released, and both clamps being retracted proximally with drive interface surfaces 77 positioned to facilitate the decoupling of clamp or jaw assembly 140 from drive linkage mechanism 170 (and hence removal of cartridge 130 from drive body 160). After release of the needle and removal of cartridge 130, the interface surfaces 77 will also remain pre-positioned for subsequent mounting of either the same cartridge or a different cartridge, as desired.

Linkage mechanism 170 can be cycled, often by actuation of handle 162 relative to drive unit body 165 of drive unit 160 so as to effect alternating grasping and releasing of a suturing needle by clamp or jaw structures 140. Drive unit interface 175 may comprise a shaft assembly including a shaft 230 which facilitates the coupling of cartridge 130 with drive unit 160 and its removal therefrom as described below. The shaft assembly of drive unit interface 175 may also comprise a column 235 through which shaft 230 is placed. Column 235 stabilizes shaft 230, generally such that shaft 230 is depressible in one direction, and also provides a stable outer surface to guide the cartridge toward a mounted position relative to drive unit 160, to engage, position, and help retain the mounted cartridge relative to the drive unit, and/or the like. In an embodiment shown by FIG. 2A, drive unit interface 175 may comprise a drive unit interface assembly. The drive unit interface assembly may be attached to drive unit body 165 through screws 232, and can be easily removed from drive unit body 165 for separate cleaning and sterilization, adjustment, and/or repair.

Figure 3:
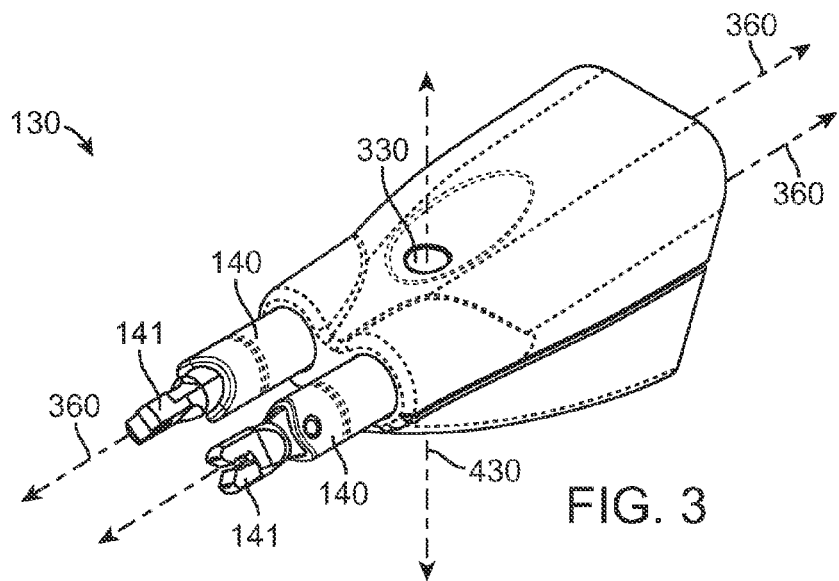
FIG. 3 shows a perspective view of an exemplary cartridge of the suturing system of FIG. 1A.
Figure 3A:
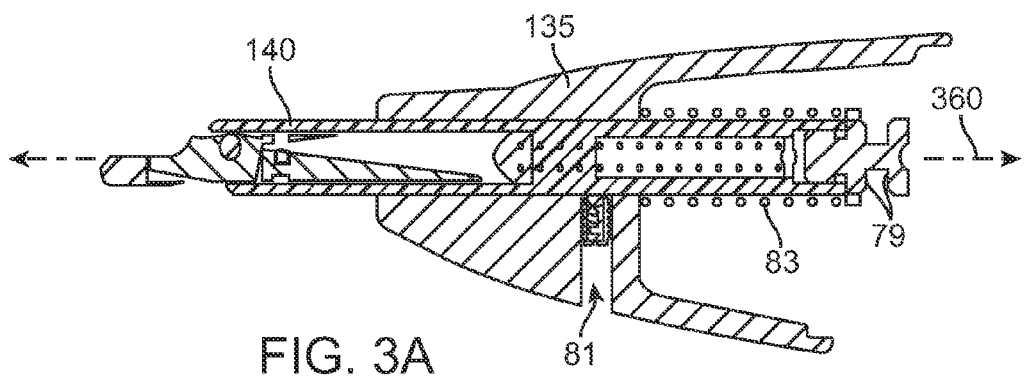
FIG. 3A shows a cross-sectional view of the cartridge of FIG. 3.

Referring now to FIGS. 3 and 3A, cartridge 130 comprises a cartridge body 135 which defines a channel 330. Cartridge 130 can be mounted over drive unit interface 175, with channel 330 axially receiving shaft 230 and column 235 along a mounting orientation shown by mounting axis 430. Clamp or jaw structures 140 comprise a pair of openable-closeable jaws 141 and are adapted to reciprocate axially along parallel reciprocation axes 360, which are transverse to mounting axis 430. Pair of jaws 141 will typically open and close as clamp or jaw structures 140 reciprocate. Clamp or jaw structures 140 can suture tissue by alternating grasping of a suture needle as described below and in co-assigned U.S. patent application Ser. No. 11/532,032, which had been previously incorporated herein by reference.

It may be advantageous to pre-position jaw assemblies 140 along axes 360 before mounting, so as to facilitate alignment of jaw interface surfaces 79 with their corresponding drive interface surfaces 77. Toward that end, a ball and detent arrangement 81 and groove 82, as shown in FIG. 3A1, may releasably hold jaw assemblies 140 at an appropriate axial position for mounting. Alternatively, a spring 83 may bias the jaw assemblies 140 to an appropriate mounting position, a lever and detent can be used, or the like. In some embodiments, the jaw assemblies may be positioned by simply tilting the cartridge and drive unit so that the jaws are angled upward sufficiently to slide the jaw assemblies proximally during mounting, thereby aligning jaw interface surfaces 79 with the released drive interface surfaces 77.

Referring now to FIGS. 4A to 4E, an exemplary mechanism by which cartridge 130 can be removably coupled to drive unit 160 is described. Cross-sectional views of suturing system 100, including cartridge 130 and drive unit 160 are shown. Cartridge 130 comprises a cartridge interface surface 145 and includes a channel 330. Drive unit interface 175 comprises shaft 230, a latch mechanism 177 coupled to shaft 230, and a spring 187. Latch mechanism 177 can pivot about pivot point 178 and comprises a latch 180 and a latch input 185. Latch mechanism 177, in particular, latch 180 of latch mechanism 177, can engage cartridge interface surface 145 of cartridge 130 to couple cartridge 130 with drive unit 160. Latch input 185 couples latch mechanism 177 to shaft 230 so that latch mechanism 177 pivots when shaft 230 is depressed. Spring 187 biases latch mechanism 177 so that it pivots back to its original position when shaft 230 is no longer depressed. Latch 180 will typically be angled such that as cartridge 130 is advanced downward along mounting axis 430 to mount cartridge 130 on drive unit 160, cartridge interface surface 145 displaces latch 180 such that latch mechanism 177 pivots without the need for shaft 230 to be depressed. Cartridge interface surface 145 will typically be hook shaped and further pressing cartridge 130 downward will eventually no longer cause cartridge interface surface 145 to displace latch 180. Latch mechanism 177 then pivots back to its original position and latch 180 captures cartridge interface surface 145.

Figure 4A:
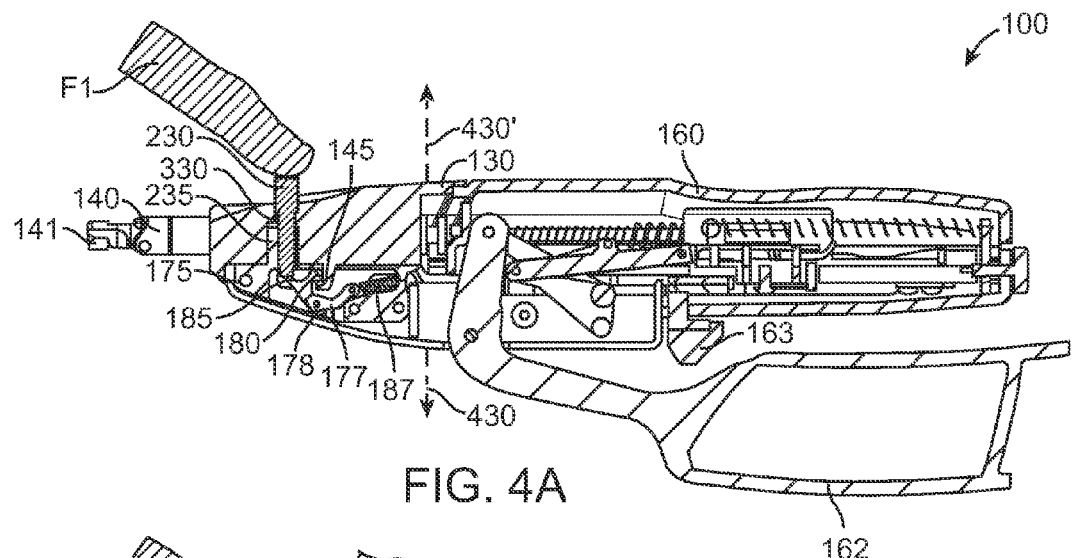
FIGS. 4A-4E show an exemplary method of removing the cartridge of FIG. 3 from the drive unit of FIG. 2.

FIG. 4A shows suturing system 100 as cartridge 130 is mounted onto drive unit 160. Latch 180 engages with cartridge interface surface 145 by hooking onto cartridge interface surface 145, thereby preventing cartridge 130 along with cartridge interface surface 145 from being moved up along mounting axis 430. Spring 187 is biased to maintain latch mechanism 177, including latch 180, in this native, latched position. Shaft 230 extends outside of channel 330.

Figure 4B:
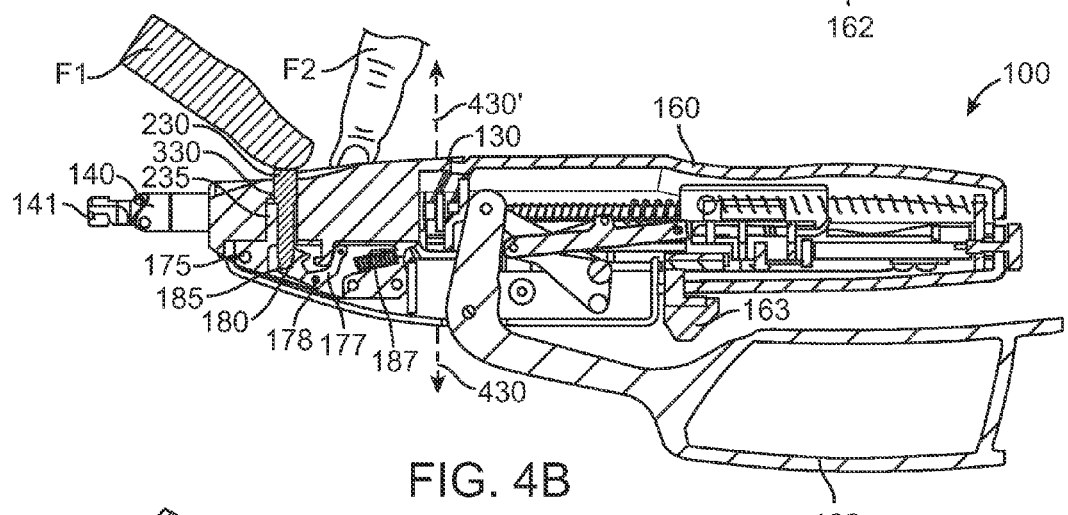
Figure 4C:
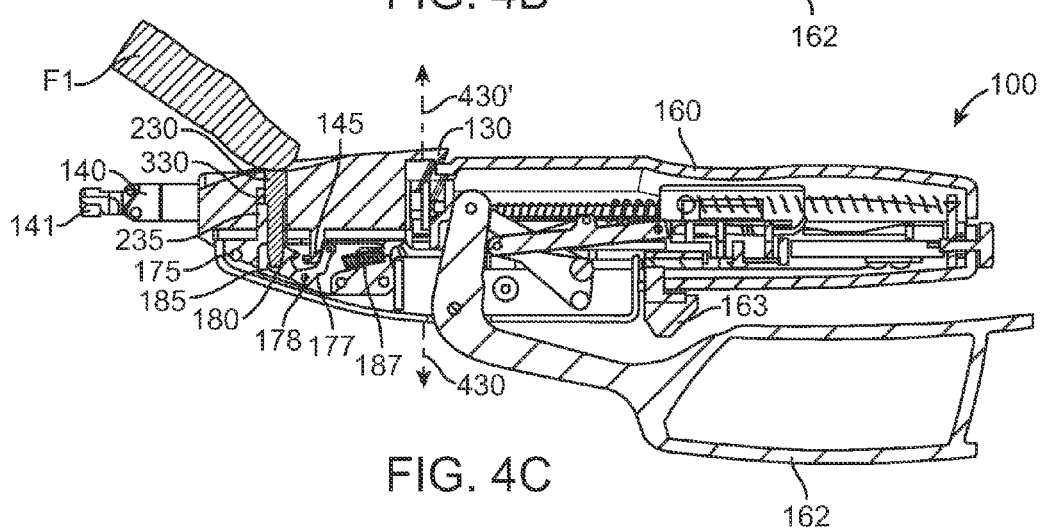
Figure 4D:
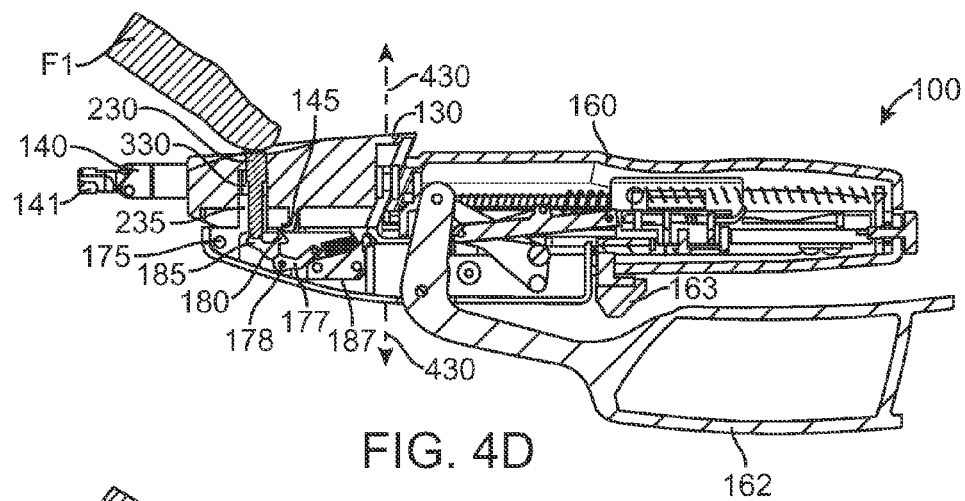
Figure 4E:
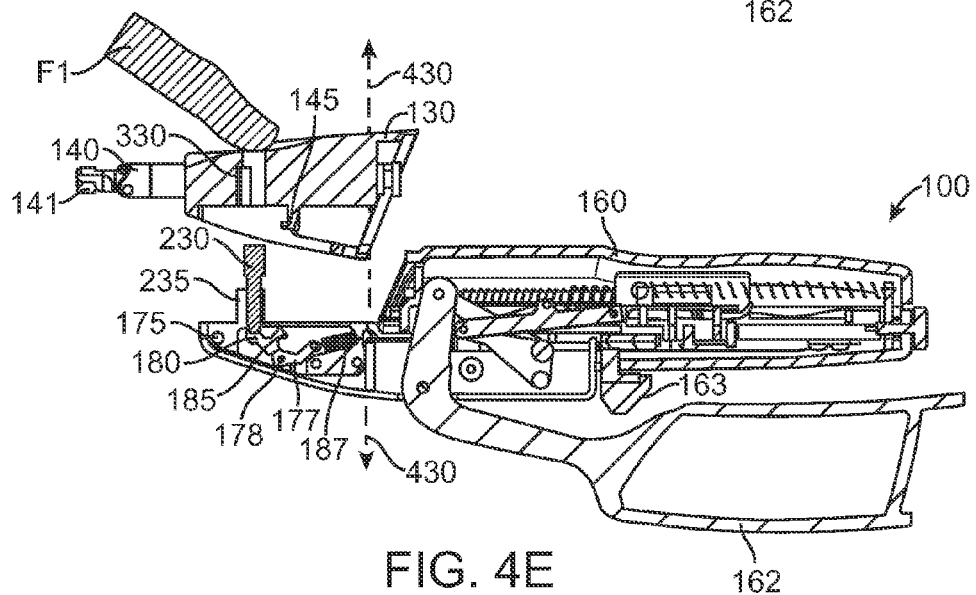

As shown in FIGS. 4B and 4C, as shaft 230 is depressed, for example, by a finger FI, latch mechanism 177 pivots into a released position from its latched position. In the released position, latch 180 no longer engages cartridge interface surface 145. This alone will typically not be sufficient for the cartridge to be disengaged from the drive unit so as to inhibit inadvertent detachment during surgery. In addition to depressing input 230 with finger FI, another force (such as one imposed using one or more other fingers Fz) may pull cartridge 130 away from drive unit 160 in a direction opposed to the mounting orientation, simultaneous with the application of force against the input. As shown in FIG. 4D, cartridge 130 can then be moved up along mounting axis 430 in a release orientation to remove cartridge 130 from drive unit 160. As shown in FIG. 4E, once cartridge 130 is removed and finger FI is no longer depressing shaft 230, latch mechanism 177 is returned to its latched position by spring 187.

Although one exemplary mechanism by which cartridge 130 can be removable coupled to drive unit 160, other latching mechanisms may be used instead. For example, cartridge 130 may instead comprise a cartridge interface comprising shaft 230 as well as latching mechanism 177, and drive unit body 165 of drive unit 160 may instead define channel 330 for axially receiving shaft 230. Also, as can be understood with reference to FIG. 1A, input 330 may be depressed and cartridge 130 moved using a single hand, such as by pressing the input with the index finger and grasping the cartridge body between the thumb and other fingers. Hence, the index (or other input actuating finger) may angle proximally away from cartridge 130 (rather than distally as shown) during mounting and/or de-coupling, and/or the cartridge may be grasped between (for example) the thumb and middle finger while they extend distally along and beyond the sides of the cartridge, while they extend proximally, or the like.

Figure 5:
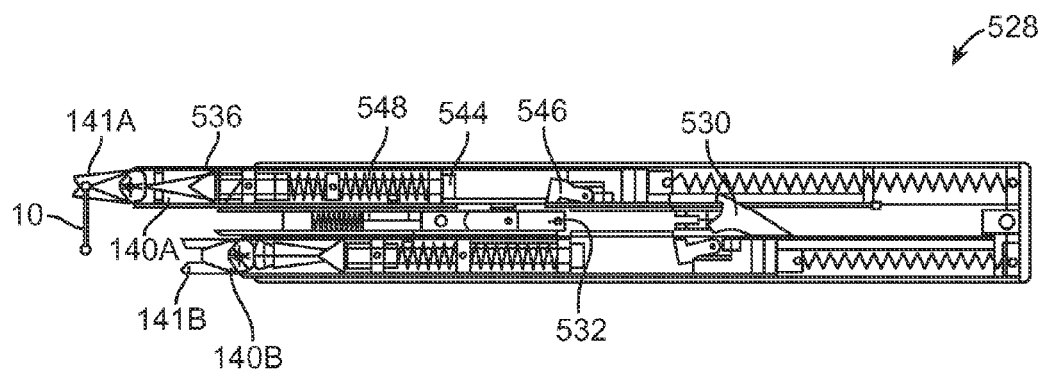
FIG. 5 shows an exemplary linkage mechanism according to embodiments of the invention.

FIG. 5 shows an exemplary drive linkage mechanism 528 by which clamp or jaw structures 140A, 140B can alternatingly grasp a needle to suture tissue. Drive linkage 528 may be used with cartridge 130 and drive unit 160 to actuate jaw structures. Drive linkage 528 includes an alternatable drive element 530 to alternatingly drive a first clamp or jaw structure 140A and then the other clamp or jaw structure 140B. Additionally, drive mechanism 528 includes an alternating latch or anchor 532 for inhibiting axial movement of the clamp that is not currently being driven. Release toggle 163 (see FIG. 2A) may optionally effect push against latch or anchor 532 so as to release the needle. Drive linkage 528 further makes use of a channel casing in which a movable tubular shaft 536 slides along its respective jaw reciprocating axis. First and second pushers and a cone with a rod 544 are disposed along a jaw reciprocating axis, while a striker 546 and a stop pin with a spring 548 are disposed off the jaw reciprocating axis. As shown in FIG. 5, an openable-closeable pair of jaws 141A of clamp or jaw structure 140A is grasping a needle 10. Movement of drive element 530 can produce axial movement of pin 548 so as to compress its spring, so the pin stops moving axially. As a result, continuing movement of drive element 530 does not produce additional movement of shaft 536, but instead causes the cone within its rod 544 to move within the shaft 536. Further movement of drive element 530 results in axial movement of the pushers, causing the striker 546 to move in alignment with a window in the shaft 536, and thus allowing the striker 546 to engage and reposition latch 532. Openable-closeable pair of jaws 141B of clamp or jaw structure 140A is also reconfigured to be in a closed position from an open position, thereby grasping needle 10. The reconfigured latch 532 inhibits proximal movement of the shaft 536 so that the handle 162 can return to an unactuated position and also so that the mechanism is now configured to actuate the other jaw structure 140B. The process can be repeated for jaw structure 140B to cause it to grasp needle 10. Further actuation of handle 162 can similarly cause pair of jaws 141A of clamp or jaw structure 140A to open, clamp or jaw structure 140B to axially retract and then axially extend, pair of jaws 141B of jaw structure 140B to close and re-grasp needle 10, repeat the same process for jaw structure 140B, and so forth. Similar drive linkage mechanism are described in co-assigned U.S. patent application Ser. No. 11/532,032, which had been previously incorporated herein by reference.

Referring now to FIGS. 6-9, the use of suturing system 100 for suturing an incision I in tissue T can be understood. Needle 10 is supported by a first clamp 140A, with the first clamp 140A grasping a proximal portion of the needle adjacent a suture S. The second clamp 140B is retracted proximally away from needle 1, so that a distal portion of the needle is free and exposed.

Figure 6:
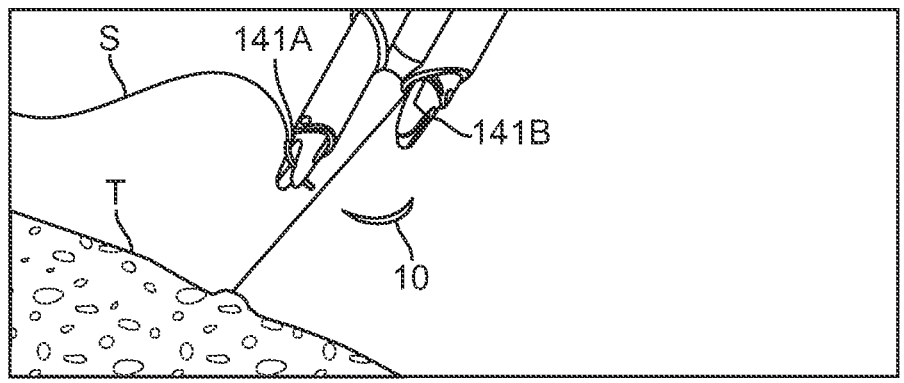
FIGS. 6-9 are perspective views showing use of the device of FIG. 1 to suture tissue.
Figure 7:
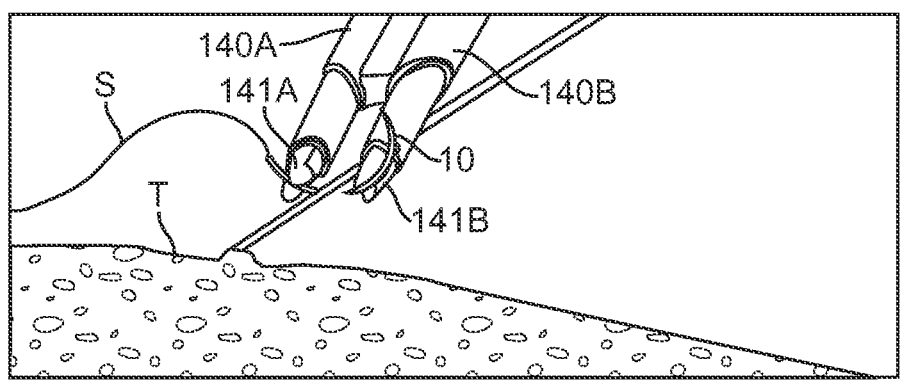
Figure 8:
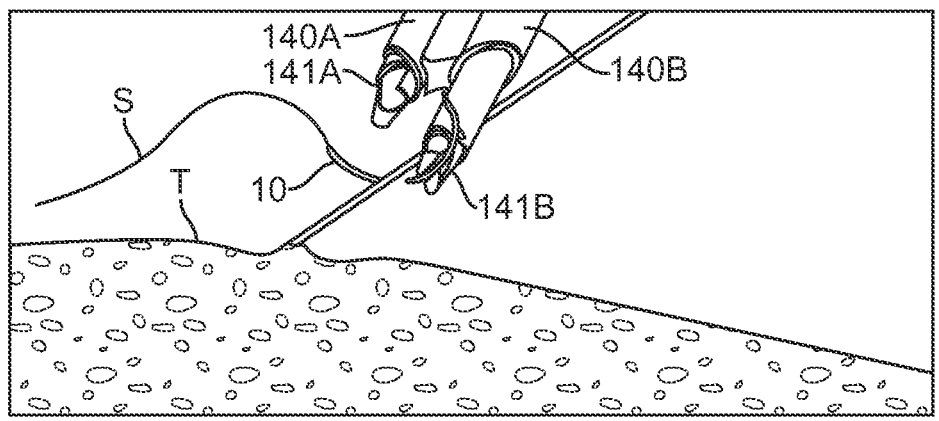

As can be understood with reference to FIG. 6, the surgeon manually moves suturing system so as to insert a distal portion of suturing needle 10 through tissue T. Advantageously, the relative movement of needle 10 relative to cartridge 130 and drive unit 160 is inhibited. This allows the surgeon to precisely control movement of the needle 10 as it is inserted through the tissue, in a manner analogous to manual manipulation of the needle using a standard needle grasper or forceps. As can be understood with reference to FIGS. 7 and 8, once the distal portion of needle 10 extends sufficiently through the tissue, clamp or jaw structures 140A and 140B can be cycled through at least a portion of their actuation cycle. Through the linkage mechanism 170, second clamp or jaw structure 140B is extended distally from the body of suturing system 100, and pair of jaws 141B of clamp or jaw structure 140B grasps the distal portion of needle 10. The first clamp or jaw structure 140A then releases needle 10 and is withdrawn proximally from around the needle 10, as illustrated in FIGS. 8 and 9.

Figure 9:
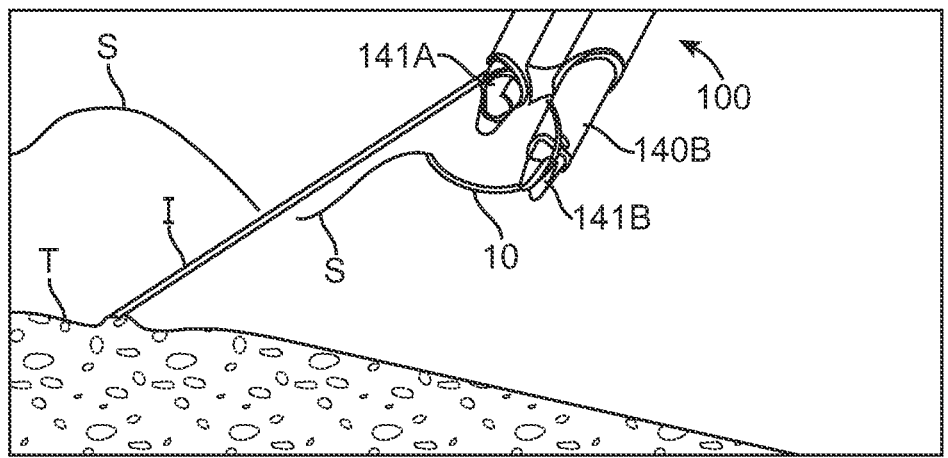

As can be understood with reference to FIG. 9, once needle 10 is held by pair of jaws 141B of clamp or jaw structure 140B, the surgeon can again manipulate the needle 10. The surgeon can move drive unit body 165 and clamp 140B to pull the proximal portion of needle 10 through tissue T, thereby leaving suture S inserted across the incision.

Prior to initiating a second stitch, the surgeon can cycle clamps or jaw mechanism 140A, 140B by opening and/or closing handle 162 through a full actuation cycle. This results in grasping of the needle 10 by first pair of jaws 141A and release of the needle 10 by second pair of jaws 141B, exposing the distal portion of the needle 10 and displacing the second clamp 140B from the needle 10 so that the needle 10 is ready to again insert through tissue T. The process can then be repeated without ever having to completely release needle 10, and by simply actuation of handle 162 after insertion of the distal portion of the needle 10 through the tissue T and again after each pulling of the needle 10 free. The process is repeated to form as many stitches as is desired. Analogous insertion of the distal portion of the needle through loops of suture, actuation of the handle, and pulling the needle free can be used to quickly and easily form knots.

As can be understood from the illustrations in FIGS. 6-9 and as described above, clamps or jaw mechanisms 140A and 140B extend distally from cartridge 130 and drive unit 160. Clamps or jaw mechanism 140A and 140B may move slightly during the actuation cycle, for example, with a clamp or jaw structure initially holding needle 10 retracting slightly as the other shaft extends, and/or with the grasping jaw structure extending slightly beyond the needle location so that a back surface of the jaws engage and stress the needle slightly to compensate for any slight misalignment. Nonetheless, each clamp or jaw structure holds the needle 10 at a fixed location while the surgeon holds the handle and inserts or withdraws the needle 10 into or from the tissue. Suturing system 100 may also be used in other ways to suture an incision in tissue, for example, as described in co-assigned U.S. patent application Ser. No. 11/532,032, which had been previously incorporated herein by reference.

Figure 10A:
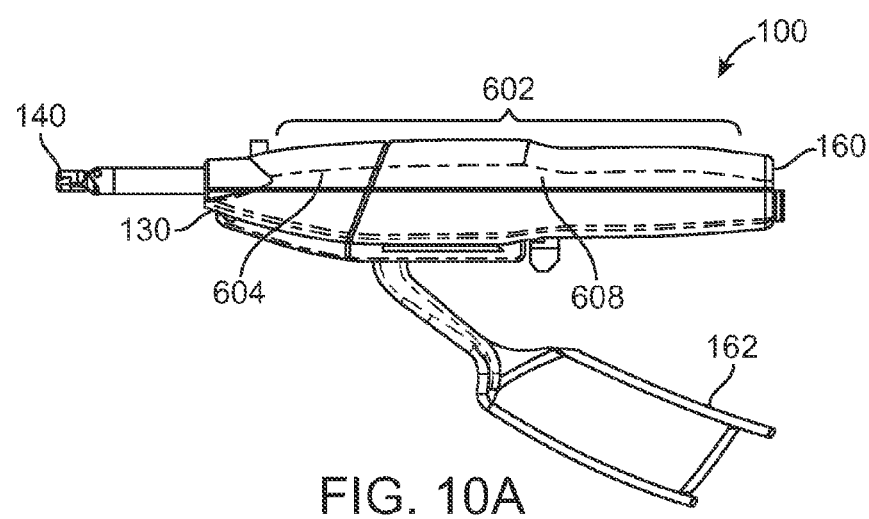
FIGS. 10A-10C are side views schematically illustrating handle surfaces of the drive unit and cartridge configured so as to allow a plurality of hand grasping positions.
Figure 10B:
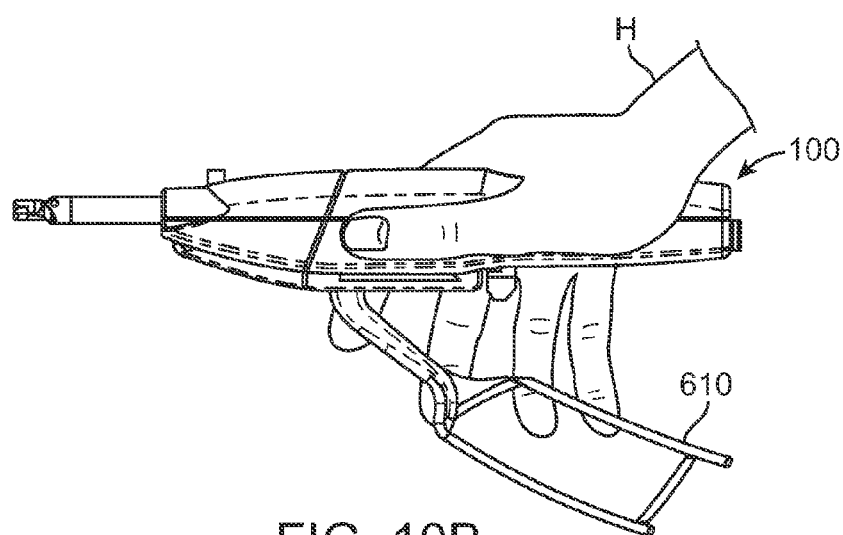
Figure 10C:
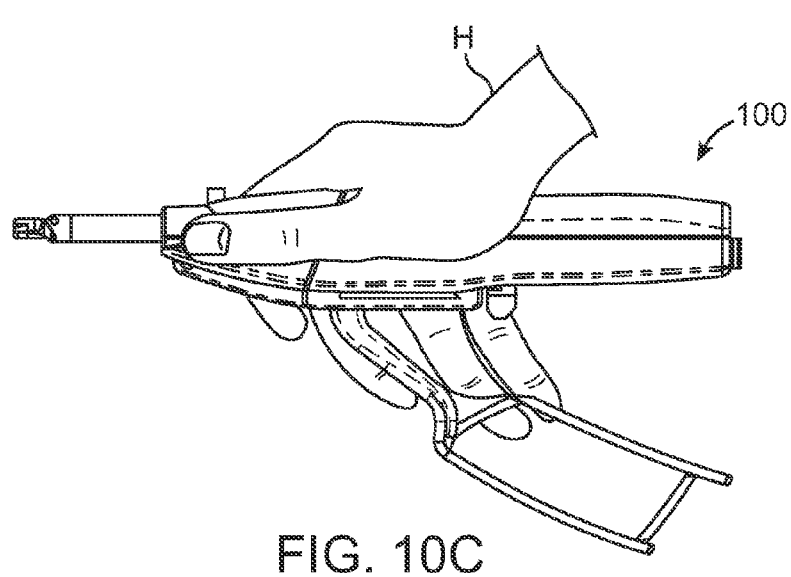

Referring now to FIGS. 10A-10C, an exemplary ergonomic handle system supporting a plurality of hand positions is shown. System 100 generally includes a fixed handle surface 602 that extends across the engaged interfaces of drive unit 160 and cartridge 130, so that a portion of the handle surface 604 is disposed on the cartridge body, and another portion of the handle surface 608 is disposed on the drive unit body. Fixed handle surface 602 may be engaged by the palm and/or thumb of the hand H of the user, with the user typically using some or all of the other fingers to engage and articulate handle 162 relative to the fixed handle surface.

As can be understood with reference to FIG. 10B, the hand may optionally be disposed somewhat proximally along the fixed handle surface, so that some or all of the fingers of the hand engage a first portion of the articulatable handle. In the exemplary embodiment, some or all of the fingers of the hand in this proximal position extend through a loop 610 of the handle 162. Alternatively, the hand may be positioned more distally (and closer to jaws 140) as illustrated in FIG. 10C, with some or all of the fingers engaging another portion of handle 162. In the exemplary embodiment some or all of the fingers engage a locally widened surface of handle 162 distally of loop 610 when the hand is in this distal position. By having the fixed handle surface extend across the interfaces and onto the cartridge, the user has the option of grasping suture system 100 as near as possible to the needle, which may be appropriate for fine suturing. In fact, rather than having surfaces which bulge out from around the cartridge, the cartridge body may optionally be faired smoothly from the interface to its distal end, thereby presenting a more distal fixed grasping surface. Also, while a slight concave proximal region is shown for engaging the hand in the proximal position, fixed handle surface 602 may be smoothly convex along its length for ergonomic grasping by a hand throughout a range of hand positions. Note that the distal hand position places a portion of the hand quite near the reciprocating shafts of the jaw assemblies, so that such a hand position may be more appropriate for open surgical suturing than for laparoscopic or other endoscopic applications. Leverage may be greater at the proximal hand position, which may ease cycling of handle 162 when placing large numbers of stitches, when manipulating larger needles, or the like.

While exemplary embodiments of the invention have been described in detail, by way of example and for clarity of understanding, a variety of modifications, changes, and adaptations will be obvious to those of skill in the art. Therefore, the scope of the present invention is limited solely by the appended claims.

What is claimed is:

1. A suturing method comprising:
   mounting a cartridge to a drive unit along a mounting orientation;
   latching the cartridge onto the drive unit;
   grasping a needle with a first jaw of the cartridge;
   cycling a linkage of the drive unit so as to alternatingly grasp the needle with the first jaw and a second jaw of the cartridge;
   detaching the cartridge from the drive unit by pushing at least one latch input and moving the cartridge away from the drive unit using motions along two opposing orientations; and advancing the latch input mounted to a shaft of the drive unit through a channel of the cartridge so that the latch input is accessible beyond the channel of the cartridge, and so that the pushing of the latch input transmits movement along the shaft to move a latch to a released position;

wherein mounting the cartridge comprises fittingly inserting the shaft of the drive unit into the channel of the cartridge until a latch mechanism moves the latch to a latched position restraining an interface of the cartridge against an interface of the drive unit.

2. The suturing method of claim 1, further comprising detaching an interface assembly from a drive unit body and the linkage of the drive unit to facilitate sterilization and/or replacement of the interface assembly independently of at least a portion of the linkage, the interface assembly including the latch mechanism.

3. The suturing method of claim 1, further comprising reciprocating the jaws along an axis transverse relative to the mounting orientation so that, when not grasping the needle, the jaws are free of tissue, and wherein the jaws alternatingly grasp a proximal portion of the needle so as to allow a needle to be inserted distally into a tissue, and a distal portion of the needle so as to allow the needle to be pulled distally from the tissue.

4. A suturing method comprising:
mounting a cartridge to a drive unit along a mounting orientation at an interface between the drive unit and the cartridge, wherein the interface comprises a shaft and column receivable within a channel;
latching the cartridge onto the drive unit by moving a latch disposed at the interface to a latched position so as to maintain engagement between the drive unit and cartridge; grasping a needle with a first jaw of the cartridge;
cycling a linkage of the drive unit so as to alternatingly grasp the needle with the first jaw and a second jaw of the cartridge; and
detaching the cartridge from the drive unit by moving the cartridge along a removal orientation opposing the mounting orientation and moving a latch input of the latch along the mounting orientation to a released position;
wherein mounting the cartridge to the drive unit comprises moving the cartridge, relative to the drive unit, along the mounting orientation which effects movement of a latching surface of the latch to the latched position as the cartridge engages the drive unit at the interface.

5. The suturing method of claim 4, wherein cycling the linkage comprises reciprocating each jaw along an associated jaw reciprocation axis, wherein each associated jaw reciprocation axis is disposed transverse to the mounting orientation.

6. The suturing method of claim 4, wherein the latch input comprises the shaft, wherein the shaft and the column are included in the drive unit at the interface, the column supporting and axially receiving a portion of the shaft, and wherein the channel is included in the cartridge at the interface with the channel extending through a cartridge body of the cartridge so that the latch input is accessible beyond the channel of the cartridge body.

7. The suturing method of claim 4, wherein the latch is included in an interface assembly detachably mounted to the drive unit to facilitate sterilization and/or replacement of the interface assembly independently of at least a portion of the linkage.

8. A suturing method comprising:
mounting a cartridge to a drive unit by engaging a latch and a shaft assembly of a drive unit interface of the drive unit within a channel of a cartridge interface of the cartridge along a mounting orientation;
latching the cartridge onto the drive unit to maintain engagement between the cartridge and drive unit along their respective interfaces by moving the latch into a latched position;
grasping a needle with a first jaw of the cartridge;
cycling a linkage of the drive unit so as to alternatingly grasp the needle with the first jaw and a second jaw of the cartridge; and
detaching the cartridge from the drive unit by articulating at least one latch input to move the latch to a released position in which the cartridge and drive unit are released, wherein articulating the at least one latch input transmits motion along the shaft assembly to the latch;
wherein detaching the cartridge from the drive unit comprises accessing the latch input through the channel of the cartridge.

9. The suturing method of claim 8, wherein detaching the cartridge from the drive unit comprises moving the cartridge relative the drive unit along a removal orientation opposing the mounting orientation.

10. The suturing method of claim 9, wherein detaching the cartridge from the drive unit comprises moving the at least one latch input along the mounting orientation such that removal of latched drive unit involves opposed motions, relative to the drive unit, of the latch input and the cartridge.

11. The suturing method of claim 8, wherein the latch is included in an interface assembly detachably mounted to the drive unit to facilitate sterilization and/or replacement of the interface assembly independently of at least a portion of the linkage.

12. The suturing method of claim 8, wherein the cartridge interface includes a latch receiving surface engageable by the latch so as to restrain the cartridge interface in engagement with the drive unit interface and so that actuation of the at least one latch input is transmitted through the channel so as to release the cartridge from the drive unit.

13. The suturing method of claim 12, wherein movement of the cartridge along the mounting orientation effects movement of a latching surface to the latched position.

14. The suturing method of claim 8, wherein the latch input is mounted to the shaft so that the latch input is accessible beyond the channel of the cartridge interface.

15. The suturing method of claim 8, wherein cycling the linkage comprises articulating a handle of the drive unit when the drive unit interface engages the cartridge unit interface with the latch in the latched position and the needle is positioned for use, the handle configured for ergonomic grasping by a hand of a user.

16. The suturing method of claim 15 further comprising:
forming a suture stitch in an open surgical environment by moving the driving unit when latched to the cartridge and articulating the handle with the hand without assistance of any other hand.

* * * * *